United States Patent [19]

Fukaya et al.

[11] Patent Number: 5,556,526
[45] Date of Patent: Sep. 17, 1996

[54] GAS SENSOR HAVING ENHANCED EXTERNAL CONNECTIVITY CHARACTERISTICS

[75] Inventors: Kenji Fukaya, Chiryu; Makoto Hori, Ogaki; Masahiro Hamaya, Anjo; Minoru Ota, Okazaki; Syuichi Nakano, Kariya; Tomoji Fukaya, Kariya, all of Japan

[73] Assignee: Nippondenso Co., Ltd., Kariya, Japan

[21] Appl. No.: 409,527

[22] Filed: Mar. 24, 1995

[30] Foreign Application Priority Data

Mar. 24, 1994 [JP] Japan .................................. 6-079334
Apr. 29, 1994 [JP] Japan .................................. 6-113969

[51] Int. Cl.⁶ .................................................. G01N 27/26
[52] U.S. Cl. ...................... 204/425; 204/426; 204/427; 174/167; 174/168; 174/169; 174/176
[58] Field of Search ........................... 204/425, 426, 204/427, 406; 174/167, 168, 169, 170, 171, 176

[56] References Cited

U.S. PATENT DOCUMENTS

| | | | |
|---|---|---|---|
| 4,588,494 | 5/1986 | Kato et al. | 204/426 |
| 4,732,663 | 3/1988 | Kato et al. | 204/427 |
| 4,818,363 | 4/1989 | Bayha et al. | 204/426 |
| 4,839,019 | 6/1989 | Takahama et al. | 204/425 |
| 4,983,271 | 1/1991 | Kato et al. | 204/426 |
| 5,238,551 | 8/1993 | Katsu et al. | 204/427 |

FOREIGN PATENT DOCUMENTS

| | | |
|---|---|---|
| 58-156845 | 9/1983 | Japan . |
| 60-150449 | 10/1985 | Japan . |
| 3-235049 | 10/1991 | Japan . |
| 5-43411 | 11/1993 | Japan . |

*Primary Examiner*—Bruce F. Bell
*Attorney, Agent, or Firm*—Cushman, Darby & Cushman

[57] ABSTRACT

A small-sized highly accurate gas sensor, which is excellent in its reliability of electric connections between contacts and fixtures while being freed from any damage, includes a base member; a detecting unit mounted on the base member for detecting a gas concentration; electrodes mounted on the detecting unit; cylindrical contacts buried integrally in an end portion of the base member; and electric leads interposed between the cylindrical contacts and the electrodes. Contacting fixtures for external lead wires are fitted in and contact the cylindrical contacts so that they are connected to the cylindrical contacts. The cylindrical contacts are formed in their openings with engaging entrances having a smaller diameter than the internal diameter, and the contacting fixtures include elastic contacting portions adapted to be diametrically reduced, when inserted into the cylindrical contacts, than the engaging entrances and expanded, after inserted, to become larger than the engaging entrances and to contact the inner walls of the cylindrical contacts.

15 Claims, 15 Drawing Sheets

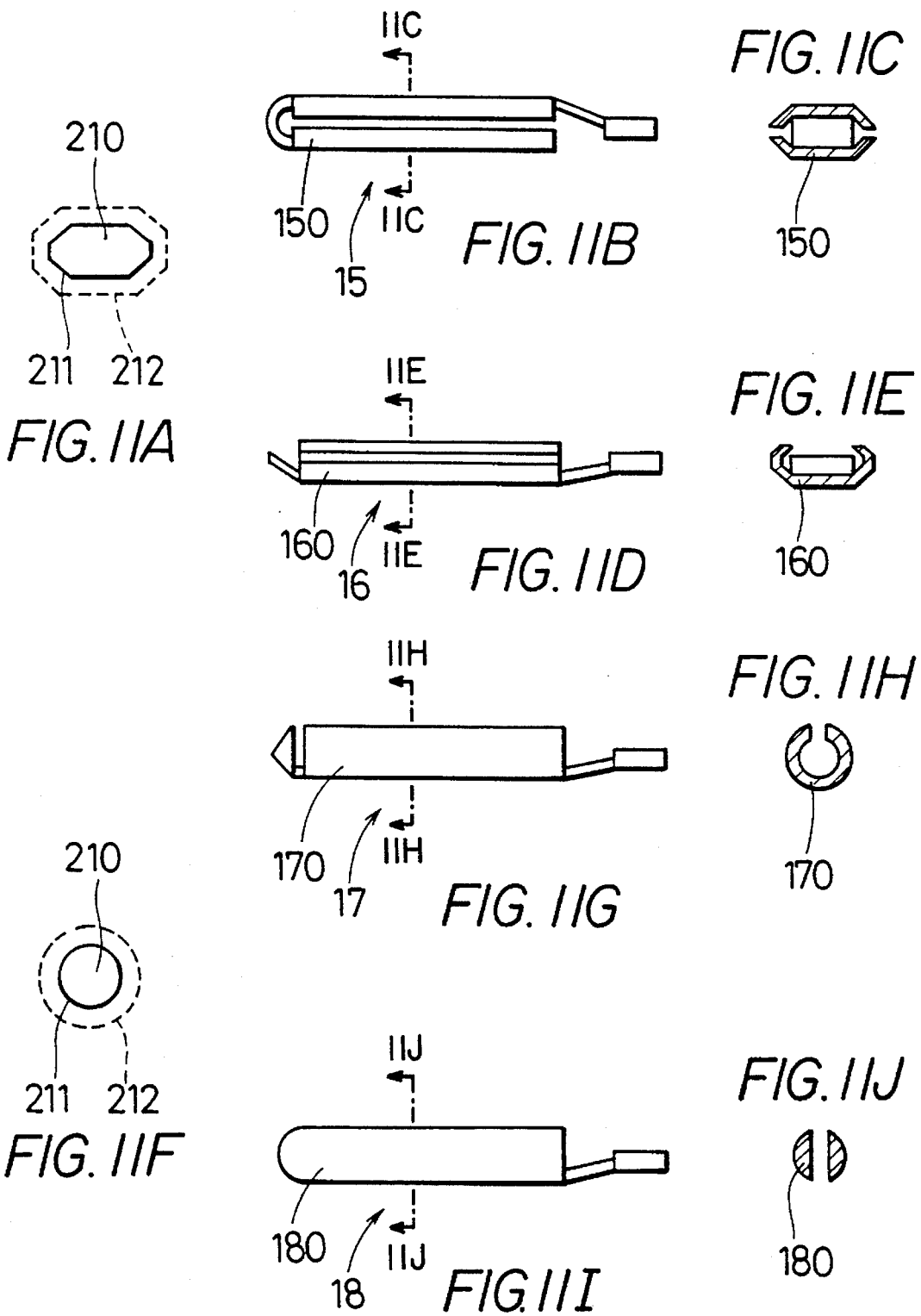

GAS SENSOR HAVING ENHANCED EXTERNAL CONNECTIVITY CHARACTERISTICS

CROSS REFERENCE TO THE RELATED APPLICATIONS

This application is based upon and claims priority from Japanese Patent Application No. Hei. 6-79334 filed Mar. 24, 1994 and Japanese Patent Application No. Hei. 6-113969 filed Apr. 29, 1994, with the contents of each document being incorporated herein by reference.

BACKGROUND OF THE INVENTION

1. Field of the Invention

The present invention relates to a gas sensor to be used for detecting an exhaust gas concentration of an internal combustion engine or the like to determine the air/fuel ratio of the exhaust gas and, more particularly, to a structure for extracting the electric signals of the sensor.

2. Description of the Related Art

The gas sensor is used to detect the exhaust gas concentration of an internal combustion engine or the like thereby to determine the air/fuel ratio of the exhaust gas so that the combustion of the internal combustion engine may be optimized.

In this gas sensor, a ceramic element molded into an elongate plate shape is accommodated in a cylindrical housing to be attached to the exhaust gas pipe. This ceramic element has its detecting unit exposed to the exhaust gas so that it is subjected at that portion to an electrochemical reaction by the exhaust gas components. The detecting unit is equipped with electrodes, through which the electric signals established by that reaction are extracted to the outside to detect the gas concentration.

In one method for extracting those signals, fixtures for contacting terminals are directly applied downward to the leading contacts which are disposed at the end portion of an elongated base member and conduct with electrodes (as disclosed in Japanese Utility Model Application Laid-Open (KOKAI) No. Sho. 60-150449).

As a second method, on the other hand, there is proposed a method in which a plurality of elongated sheets including the base member are laminated and are recessed at one end with recesses for preventing the contacting terminal fixtures from coming out, so that the electric signals may be reliably extracted from the base member (as disclosed in Japanese Patent Application Laid-Open (KOKAI) No. Hei. 3-235049).

In a third method, as shown in FIGS. 21 and 22, contact plates 971 attached to lead wires 97 are thrust through insulating members 973 onto electric terminal portions 911 by the actions of leaf springs 974.

According to this method, the leaf springs 974, the insulating members 973 and the contact plates 971 are sequentially arranged between a cover 950 and an oxygen detecting element, and the cover 950 is thrust from a broken-line position to a solid-line position, as shown. Moreover, the contact plates 971 are thrust onto the electric terminal portions 911 of the oxygen detecting element 91 by the elastic repulsions of the leaf springs 974.

According to the aforementioned first method, however, the base member has its end portion exposed to the thrust of the contacting terminal fixtures so that it is liable to be damaged with a crack or the like by the bending force to have an insufficient strength. The adjoining contacting terminal fixtures are liable to contact and accordingly to short. In case, moreover, a number of contacts are to be provided, they cannot be given a sufficient area and thereby effect an imperfect contact between the contacting terminal contacts and the contacting terminal fixtures.

According to the third method, on the other hand, a transverse load (i.e., a load perpendicular to the axis) is applied at assembling time or the like to the oxygen detecting element 91 to raise a problem that the oxygen detecting element 91 is liable to be broken.

SUMMARY OF THE INVENTION

In view of the problems of the prior art thus far described, therefore, the present invention contemplates to effect the electric connections of a gas sensor between the electric terminal portions and the external connection member by a contact method of feasible assembly and to provide a gas sensor having a high contact reliability.

In the gas sensor of the present invention, the cylindrical contacts are integrally buried in the end portion of a base member. As a result, this base member can fix the cylindrical contacts without fail. Thus, the base member absorbs the thrust coming from the contacting fixtures which are fitted in and contacted with the cylindrical contacts, thereby diffusing the thrust into the entirety of the base member (as shown in FIG. 6). As a result, the base member is freed from damage such as a crack or fracture.

Since, moreover, the cylindrical contacts are integrally buried in the base member, their buried positions can be set in advance. As a result, the cylindrical contacts and the contacting fixture can be highly accurately contacted at desired positions. In case, moreover, the base member is equipped at its one end with a plurality of cylindrical contacts, these cylindrical contacts are kept from contacting with each other. In the present invention, moreover, the contacting fixtures are fitted in and contacted with the engaging entrances of the cylindrical contacts. As a result, sufficient contact areas can be retained between the cylindrical contacts and the contacting fixtures.

As a result, the cylindrical contacts and the contacting fixtures can be reliably connected to enhance the reliability in their electric connections.

Moreover, the connections between the cylindrical contacts and the contacts need not resort to a troublesome process such as the soldering process so that the number of assembling steps can be reduced.

As described above, according to the present invention, it is possible to provide an oxygen detecting element which has its electric terminal portions electrically connected with an external connection member by the contact method allowing a feasible assembly and which has a high contact reliability.

The electric terminals portions are inclined with respect to the axis so that the contacts thrust toward the leading end are reliably contacted at the sloped portions of the electric terminal portions. Even if, moreover, the electric terminal portions or the contacts are deformed due to aging, they are thrust by the thrust member to establish new contacting portions without fail on the slopes of the electric terminal portions.

As described above, the electric terminal portions and the contacts are held in stable contact in high reliability for a long term.

BRIEF DESCRIPTION OF THE DRAWINGS

FIGS. 11A–11J are explanatory views of engaging entrances and various contacting fixtures of Embodiments 4 and 5;

DETAILED DESCRIPTION OF THE PRESENTLY PREFERRED EXEMPLARY EMBODIMENTS

Embodiment 1

A gas sensor according to a embodiment of the present invention will be described with reference to FIGS. 1 to 6.

Figure 1:
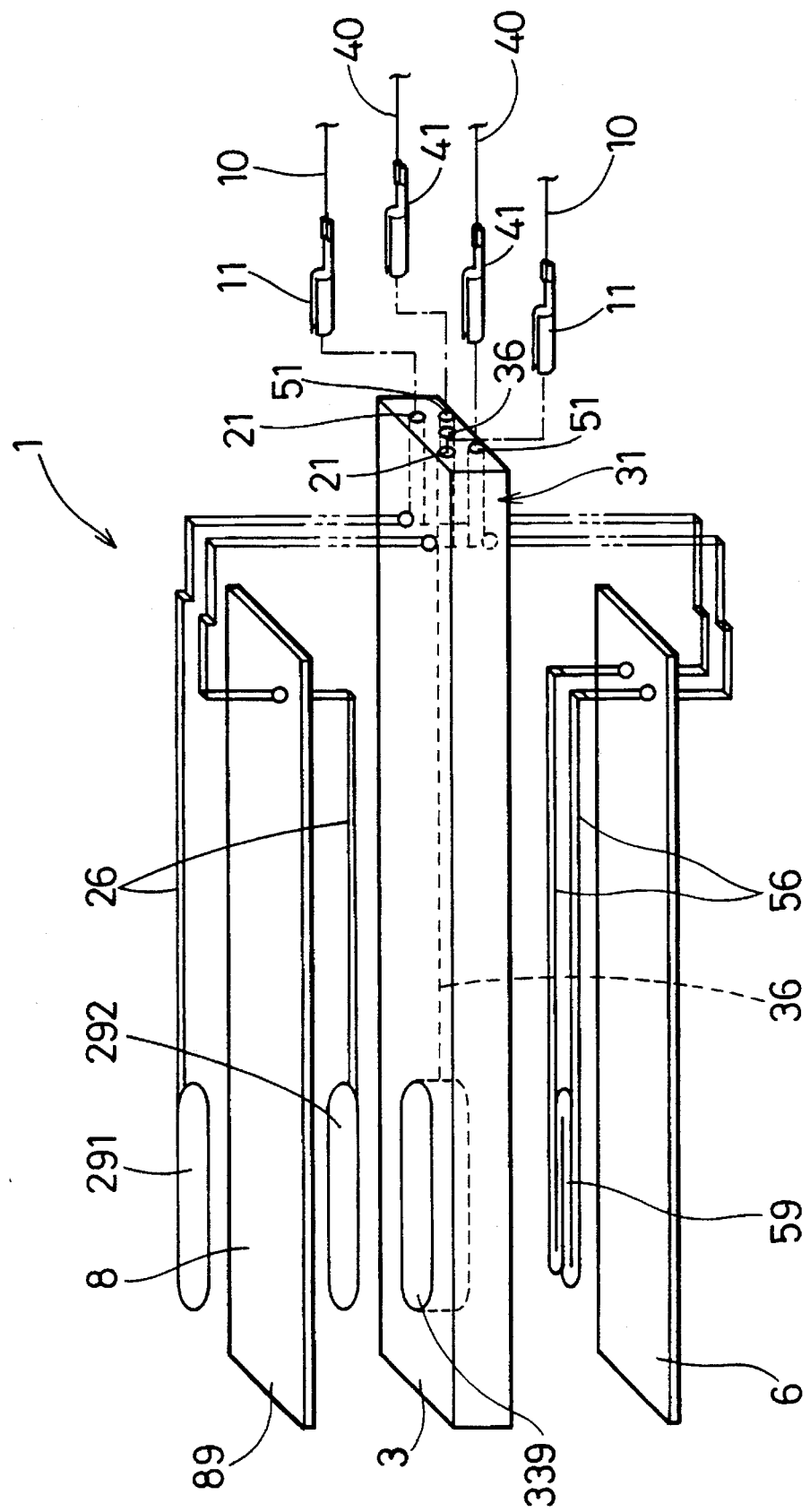
FIG. 1 is an explanatory view of a sensor element of Embodiment 1.

The gas sensor of this embodiment has a sensor element 1 packaged therein, as shown in FIG. 1. This gas element 1 is composed of: a base member 3; a detecting unit 8 mounted on the base member 3 for detecting a gas concentration; electrodes 291 and 292 individually mounted on the two faces of the detecting unit 8; and two cylindrical contacts 21 integrally buried in the end portion 31 of the base member 3. The two cylindrical contacts 21 and the electrodes 291 and 292 are individually connected by electrode leads 26.

In the cylindrical contact 21, there is fitted and contacted a contacting fixture 11 which is connected with an external lead wire 10. With the end portion of the contacting fixture 11, there is connected one end of the external lead wire 10 by a caulking connector 111.

Figure 2:
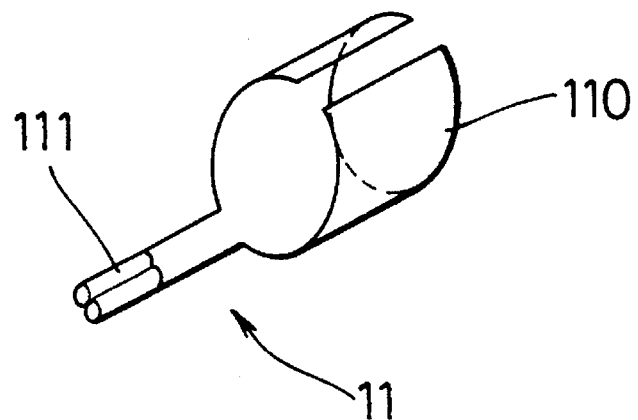
FIG. 2 is a perspective view of a contacting fixture of Embodiment 1.
Figure 3:
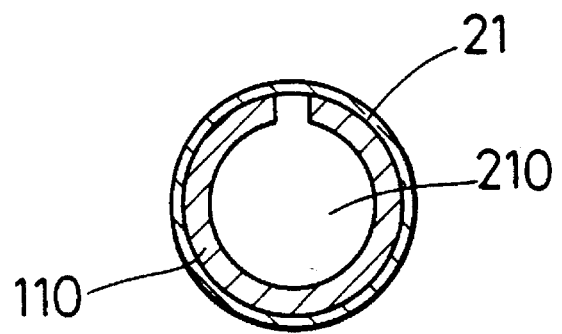
FIG. 3 is an explanatory view showing a fitting/ contacting state between a cylindrical contact and the contacting fixture of Embodiment 1.

The contacting fixture 11 is equipped at its leading end portion with an elastic contact portion 110, as shown in FIG. 2. On the other hand, the trailing end portion is equipped with the caulking connector 111 for caulking the external lead wire. The elastic contact portion 110 is formed generally into a cylindrical shape, and is curved to have a section of letter "C". The elastic contact portion 110 is given in a free state a diameter slightly larger than that of the aforementioned cylindrical contact. As shown in FIG. 3, the elastic contact portion 110 has its contact face elastically contacted with and closely fixed in the cylindrical contact 21 by its elastic thrust.

Figure 5:
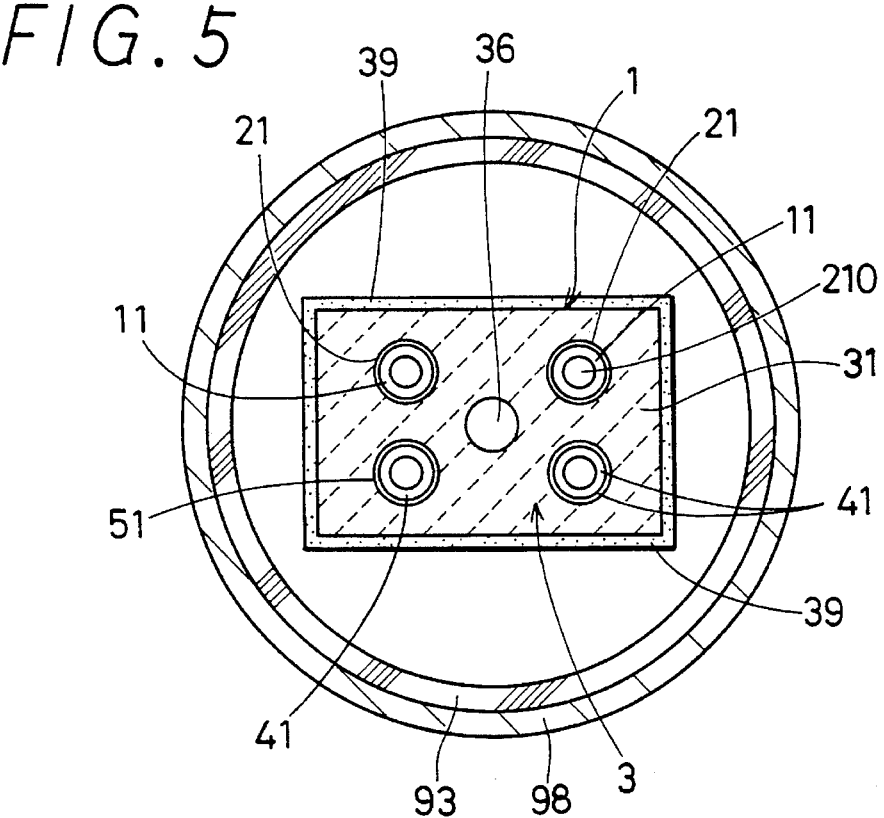
FIG. 5 is a section view taken in the direction of arrow IV—IV of FIG. 4.

As shown in FIGS. 1, 3 and 5, the cylindrical contact 21 is formed into a cylindrical shape having a hollow engaging entrance 210 therein. In this engaging entrance 210, there is fitted the contacting fixture 11 to contact the aforementioned cylindrical contact 21.

This cylindrical contact 21 is integrally buried in the end portion 31 of the base member 3 by an injection molding process.

In the end portion 31 of the base member 3, on the other hand, there are opened two later-described heater contacts 51 and ventilation hole 36, as shown in FIG. 1, in addition to the aforementioned cylindrical contact 21. In the heater contact 51, as in the aforementioned cylindrical contact 21, there is fitted a contacting fixture 41 which is connected with an external lead wire 40. This contacting fixture 41 is given a construction similar to that of the contacting fixture 11 shown in FIG. 2 and is connected with the external lead wire 40 by the caulking connector.

In the construction described above, the cylindrical contact 21 is used for extracting signals, whereas the heater contact 51 is used for supplying an electric current for the heater. Moreover, these two contacts are made to have identical structures as the cylindrical contact and are connected with the external lead wires by the caulking connectors.

The base member 3 is formed with: a duct 339, which is located at the position of the electrodes 291 and 292, and the ventilation hole 36 communicating with the duct 339. The ventilation hole 36 leads through the inside of the base member 3 and is opened at the end portion 31. The ventilation hole 36 introduces the atmosphere into the duct 339. The atmosphere thus introduced is guided to the detecting unit 8.

Figure 4:
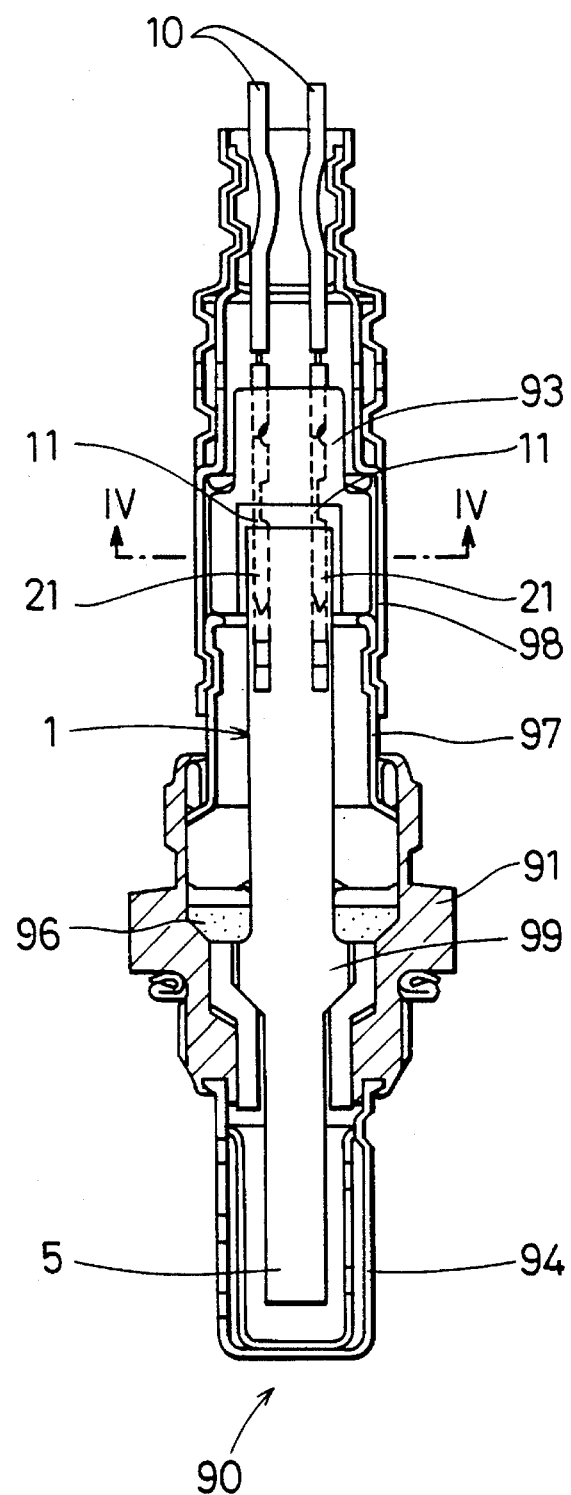
FIG. 4 is a sectional view of a gas sensor of Embodiment 1.

The base member 3 is molded to have an elongated plate shape by injecting a highly strong insulating ceramic material such as alumina. The base member 3 has its central portion formed at its two side faces with angle protrusions 99, as shown in FIG. 4, for vertically positioning the base member.

The engaging entrances of the cylindrical contacts 21 and the heater contacts 51, and the duct 339 and the ventilation hole 36 of the base member 3 are formed simultaneously as the base member 3 is injection-molded, The cylindrical contacts 21 and the heater contacts 51 are printed on the inner wall of the engaging entrance by an ordinary internal printing method such as the brushing method.

The detecting unit 8 is equipped, as shown in FIG. 1, with a solid electrolyte sheet 89 of zirconia. Specifically, this detecting unit 8 is prepared by integrating laminating at least one set of solid electrolyte sheets 89. This solid electrolyte sheet 89 is arranged on its two surfaces with at least one pair of electrodes 291 and 292.

At the detecting unit 8, a concentration electromotive force depending upon the exhaust gas concentration and an oxygen ion pumping current are generated and are received as electric signals by the electrodes 291 and 292. The electric signals thus received are guided to the electrode leads 26 and the cylindrical contacts 21 and are transferred to the contacting fixture 11. Then, the electric signals are lead out through the external lead wires 10 to the outside of a gas sensor 90.

On the lower face of the base member 3, there is mounted a heater 59. This heater 59 is fixed on a heater substrate 6 made of highly pure alumina.

The heater 59 heats the detecting unit 8 to promote an electrochemical reaction by the gas components. The heater 59 is connected through heater leads 56 with the two heater contacts 51 which are buried in the end portion 31 of the base member 3. The current is introduced into and out of the heater 59 through the heater contacts 51.

The heater contacts 51 are formed like the aforementioned cylindrical contacts 21 into the cylindrical shapes having the internal engaging entrances, in which are fitted and contacted the heater contacting fixtures 41. These heater contacting fixtures 41 are shaped like the aforementioned contacting fixtures 11 to have their end portions connected with the external lead wires 40. The sensor element 1 has its surface coated with a protective film 39 made of a large surface area ceramic material, as shown in FIG. 5.

The sensor element 1 is fixed in a cylindrical housing 91 made of metal, as shown in FIG. 4. This housing 91 has its lower open portion covered with a bottomed double-cylinder protective cover 94 which is formed with a number of ventilation holes. The aforementioned detecting unit 5 is arranged in the protective cover 94.

The housing 91 is lined with an insulating member 96 along its inner circumference. In the upper open portion of the housing 91, there is fixed a body cover 97. This body cover 97 is capped by a dust cover 98. This dust cover 98 is arranged therein with a cylindrical insulator 93 of ceramics, as shown in FIGS. 4 and 5. In this ceramic insulator 93, there are housed and positioned the aforementioned contacting fixtures 11 and 41.

The aforementioned sensor element 1 is extended through the protective cover 94, insulating member 96, body cover 97 and dust cover 98.

Here will be described the operations and effects of the present embodiment in the following.

In the gas sensor of the present embodiment, as shown in FIG. 1, the cylindrical contacts 21 are integrally buried in the end portion 31 of the base member 3. As a result, this base member 3 can fix the cylindrical contacts 21 without fail. Thus, the base member 3 absorbs the thrust coming from the contacting fixtures 11, which are fitted in and contacted with those cylindrical contacts, and diffuses the thrust into the entirety of the base member 3. As a result, the base member 3 is free from any damage such as a fracture or crack.

Thanks to the cylindrical shape, the cylindrical contacts 21 can be mounted at one end of the base member 3 with a small space and at a short distance. In addition, the cylindrical contacts 21 need no separate members for mounting them, unlike the prior art. Thus, the gas sensor can be small-sized.

On the other hand, the base member 3 is made of a ceramic insulating member. This makes it unnecessary to especially insulate the aforementioned various functional members which are mounted on the base member 3.

On the other hand, the cylindrical contacts 21 are integrally buried in the base member 3 so that their burying positions can be set in advance. As a result, the cylindrical contacts 21 and the contacting fixtures 11 can be highly accurately contacted at the preset positions.

Figure 6:
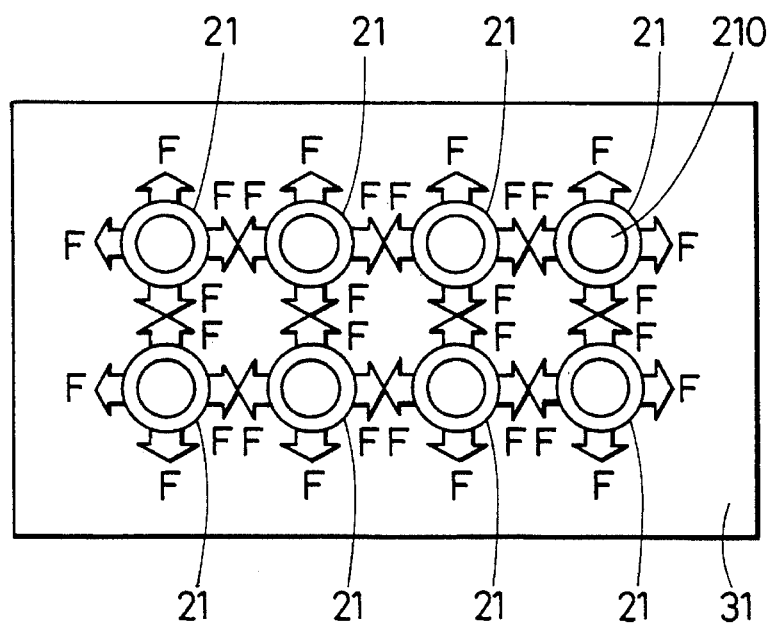
FIG. 6 is an explanatory view showing the operations and effects of Embodiment 1.

As shown in FIG. 6, on the other hand, the thrust F from a contacting fixture is offset by the thrust F of an adjoining contacting fixture. As a result, the cylindrical contacts 21 can be disposed so close to each other as to retain the electric insulation.

As shown in FIG. 3, on the other hand, the elastic contact portion 110 of the contacting fixture is fitted in and contacted with the engaging entrance 210 of the cylindrical contact 21. As a result, the cylindrical contacts 21 and contacting fixtures 11 can retain their sufficient contacting areas so that they can be connected without fail.

As shown in FIG. 1, on the other hand, the size of the base member 3 can be present by the mold to be used for the injection molding process so that it can have a highly sizing accuracy. Moreover, the cylindrical contacts 11 are fitted under uniform thrusts in the cylindrical contacts 21 which are buried in the base member 3. This enhances the reliability of the electric connections between the cylindrical contacts and the contacting fixtures.

On the other hand, the heater contacts 51 are given a structure similar to that of the aforementioned cylindrical contacts and are mounted in the end portion 31 of the base member 3. As a result, the heater contacts are excellent like the cylindrical contacts in the reliability of connection with the contacting fixtures. Moreover, the size of the gas sensor can be further reduced.

Comparison Example

Figure 7:
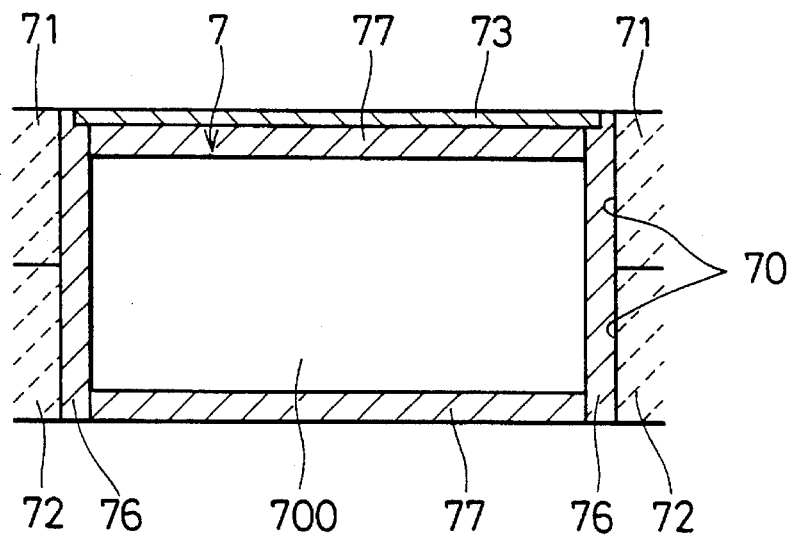
FIG. 7 is an enlarged view of a portion of the end portion of a base member and shows a contacting state between the cylindrical contact and the contacting fixture of a comparison example.

In the present comparison example, as shown in FIG. 7, the base member is prepared by laminating a plurality of sheets 71 and 72 having slits 70 for forming an engaging entrance 700. Above the engaging entrance 700, there is arranged a contact 73. This contact 73 is given a flat plate shape and is mounted on the sheet 71. In the engaging entrance 700, there is inserted a fixture 7 (which is identical to a contacting fixture 13 of FIG. 9) having a vertically elastic contact portion 77 to contact the contact 73 above the engaging entrance 700 and the elastic contact portion 77.

As a result, in the present comparison example, the contact 73 contacts only one face of the fixture 7 and has a small contacting area. On the other hand, the plurality of sheets 71 and 72 may be displaced. In order to keep the shape of the retaining entrance 700 at this time, the engaging entrance 700 has to be arranged with a displacement stopping member 76. On the other hand, the base member is difficult to have its thickness controlled because it is a laminate of the plurality of sheets.

In the gas sensor of the foregoing Embodiment 1, on the contrary, the disadvantages of the present example are not caused because the contacts are integrally molded of the base member and because the contacts are made cylindrical.

Embodiment 2

Figure 8:
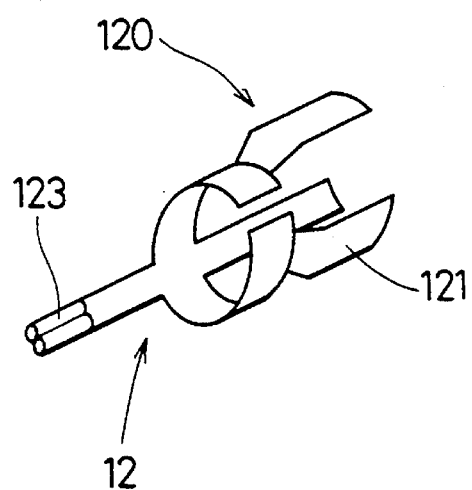
FIG. 8 is a perspective view of a contacting fixture of Embodiment 2.

In the present embodiment, as shown in FIG. 8, a contacting fixture 12 has its elastic contact portion 120 formed with a bulging portion 121. The cylindrical contact has its inside contoured to conform to the shape of the elastic contact portion 120. The contacting fixture 12 has its end portion connected with one end of an external lead wire by a caulking connector 123.

In the present embodiment, in the elastic contact portion 120 having the bulging portion 121, there is fitted and contacted a cylindrical contact which has a contour conforming to the shape of the former. As a result, the bulging portion comes into close contact with the cylindrical contact so that the contacting fixture is freed from coming out of the cylindrical contact. In addition, effects similar to those of Embodiment 1 can be achieved.

Embodiment 3

In the present embodiment, as shown in FIGS. 9 and 10, the engaging entrance 210 of the cylindrical contact is given a rectangular shape which is formed with an opening having a smaller size than that of the inside 212. This engaging entrance 210 is coated all over its inner wall with the not-shown cylindrical contacts. In the engaging entrance 210, there is fitted and contacted the contacting fixture 12 which has the elastic contacting portion 120 having a rectangular shape conforming to that of the engaging entrance 210. The elastic contacting portion 120 is contacted at its four sides with the cylindrical contact coating the engaging entrance.

Figure 10A:
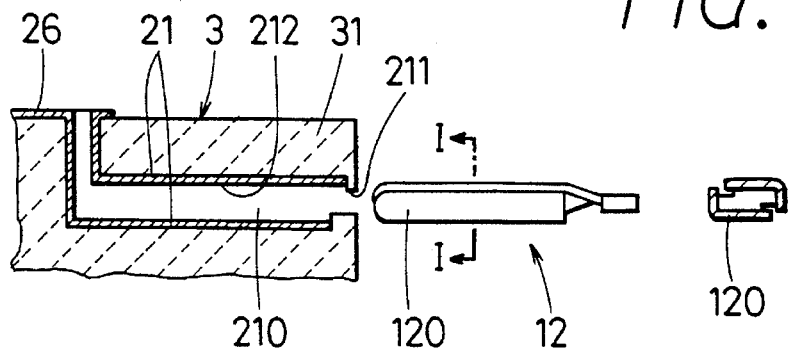
FIGS. 10A–10F are an explanatory view showing a fitting method of the contacting fixture of Embodiment 3.
Figure 10B:
Figure 10C:
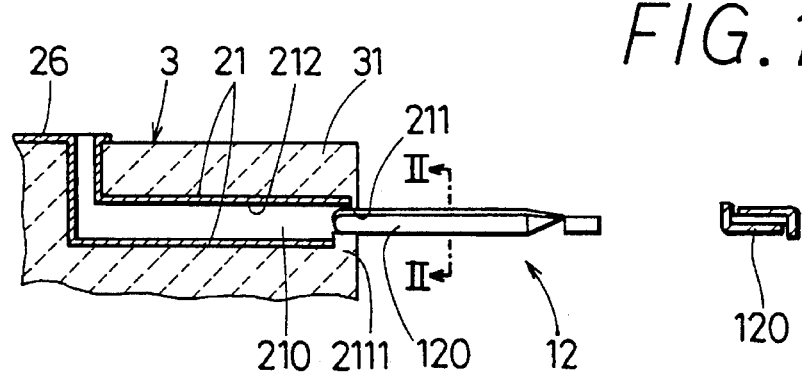
Figure 10D:
Figure 10E:
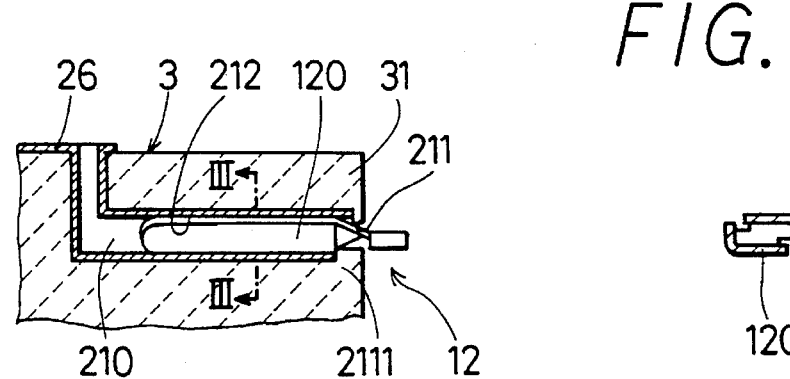
Figure 10F:
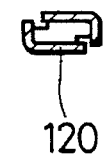

The elastic contacting portion 120 is made of a spring material and is slightly larger in a free state than the engaging entrance 210, as shown in FIG. 10A. When the elastic contacting portion 120 is to be inserted into the engaging entrance 210, it is vertically depressed to become thinner by the bulging portion 2111 of the opening 211, as shown in FIG. 10C. The contacting fixture 12 is further forced into the engaging entrance 210 to insert the elastic contacting portion 120 to its full length.

Then, the elastic contacting portion 120 expands in the opening 211 of the engaging entrance 210 to come into engagement with the bulging portion 2111. As a result, the elastic contacting portion 120 comes into close contact with the cylindrical contact 21 covering the engaging entrance 120. On the other hand, the contacting fixture 12 does not chatter. Since, moreover, the elastic contacting portion 120 engages with the bulging portion 2111 of the opening, the contacting fixture 12 will not come out of the cylindrical contact 21 in the least.

Figure 9A:
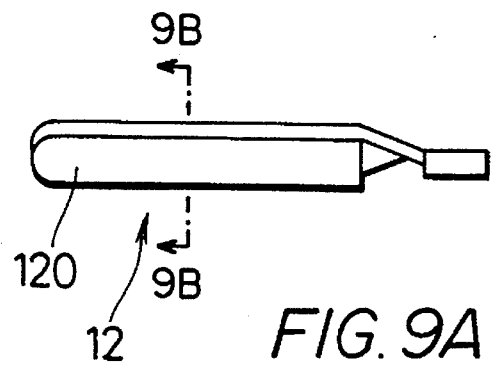
FIGS. 9(a)–9(g) are explanatory views of an engaging entrance and various contacting fixtures of Embodiment 3.
Figure 9B:
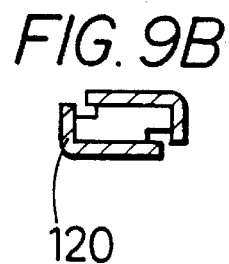
Figure 9G:
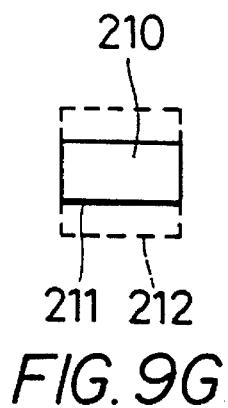
Figure 9C:
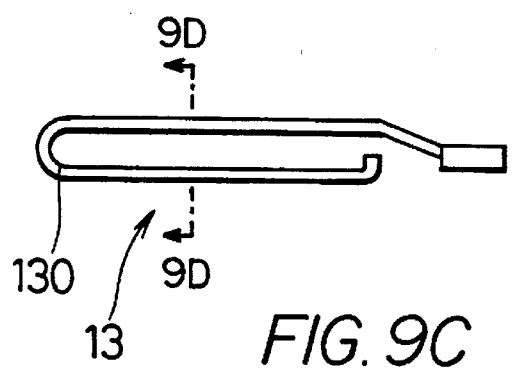
Figure 9D:
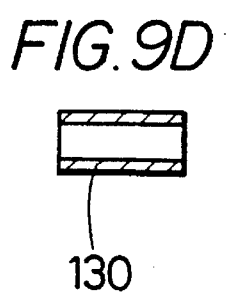
Figure 9E:
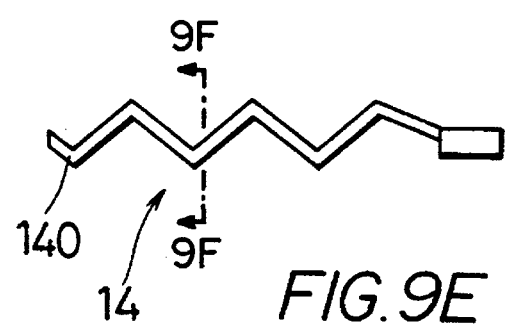
Figure 9F:
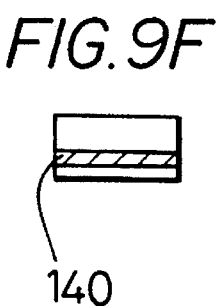

As shown in FIG. 9C and 9D, on the other hand, not only the aforementioned contacting fixture 12 but also the contacting fixture 13 having an elastic contacting portion 130 made of a clip-shaped sheet and a contacting fixture 14 (FIGS. 9E and 9F) a bellows-shaped elastic contacting portion 140 can be fitted in the engaging entrance 210.

The remaining portions are similar to those of Embodiment 1.

The present embodiment can also achieve the effects as those of Embodiment 1.

Embodiment 4

In the present embodiment, as shown in FIG. 11A, the engaging entrance 210 of the cylindrical contact is formed into a flattened octagonal shape.

In the engaging entrance 210, there is fitted and contacted a contacting fixture 15 which has an elastic contacting portion 150 having a shape conforming to that of the engaging entrance 210. The elastic contacting portion 150 is shaped by bending a long sheet in a clip shape and by curving the two end portions in a boat shape along the contour of the engaging entrance as shown in FIGS. 11B and 11C. The elastic contacting portion 150 contacted at its upper and lower faces with the cylindrical contact coating the engaging entrance.

In the engaging entrance 210, moreover, there may be fitted and contacted a contacting fixture 16 having a C-shaped elastic contacting portion 160 as shown in FIGS. 11D and 11E.

The remaining portions are similar to those of Embodiment 3.

The present embodiment can also achieve the effects as those of Embodiment 3.

Embodiment 5

In the present embodiment, as shown FIG. 11F, the engaging entrance 210 of the cylindrical contact is given a cylindrical shape.

In the engaging entrance 210, there is fitted and contacted a contacting fixture 17 which has an elastic contacting portion 170 having a shape conforming to that of the engaging entrance 210 as shown in FIGS. 11G and 11H. The elastic contacting portion 170 is contacted substantially all over the surface with the cylindrical contact coating the engaging entrance 210.

In the engaging entrance 210, moreover, there may be fitted and contacted a contacting fixture 18 which has a pair of transverse elastic contacting portions 180 as shown in FIGS. 11I and 11J.

The remaining portions are similar to those of Embodiment 3.

The present embodiment can also achieve the effects as those of Embodiment 3.

Embodiment 6

Figure 12A:
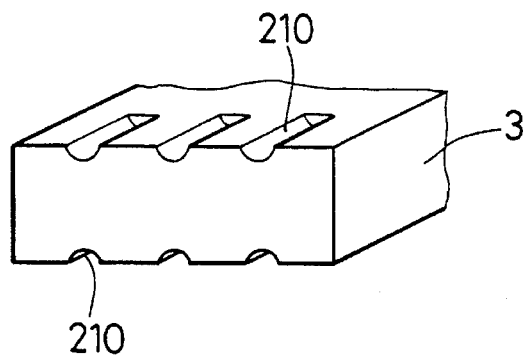
FIG. 12A–12C are an explanatory view of an engaging entrance of Embodiment 6.
Figure 12B:
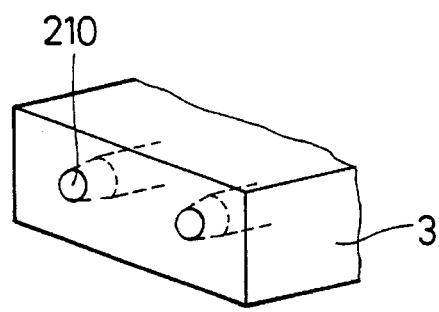
Figure 12C:
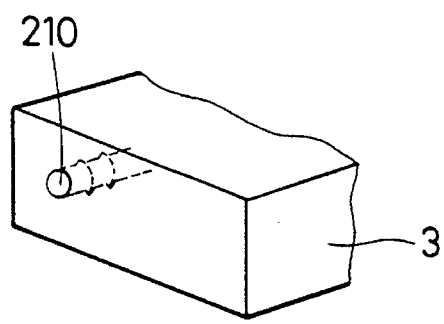

In the present embodiment, as shown in FIG. 12, there are enumerated a variety of shapes for the engaging entrance 210. Specifically, this engaging entrance 210 is exemplified by a semi-cylindrical shape formed in the surface of the base member 3 (as shown in FIG. 12A), by a generally cylindrical shape having an opening of a reduced diameter (as shown in FIG. 12B), or by a rugged cylindrical shape (as shown in FIG. 12C). In each of the various engaging entrances 12, there is fitted and contacted the contacting fixture which has a shape conforming to the shape of the former.

The remaining portions are similar to those of Embodiment 1.

The present embodiment can also achieve the effects as those of Embodiment 1.

Embodiment 7

Figure 13:
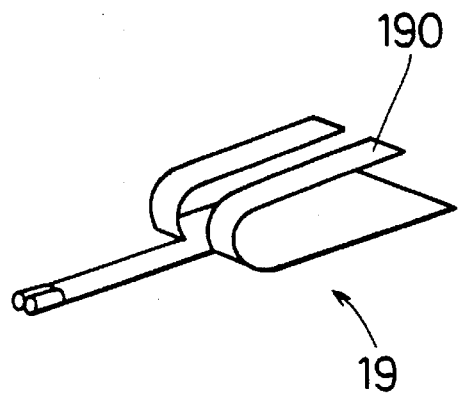
FIG. 13 is a perspective view of a contacting fixture of Embodiment 7.
Figure 14:
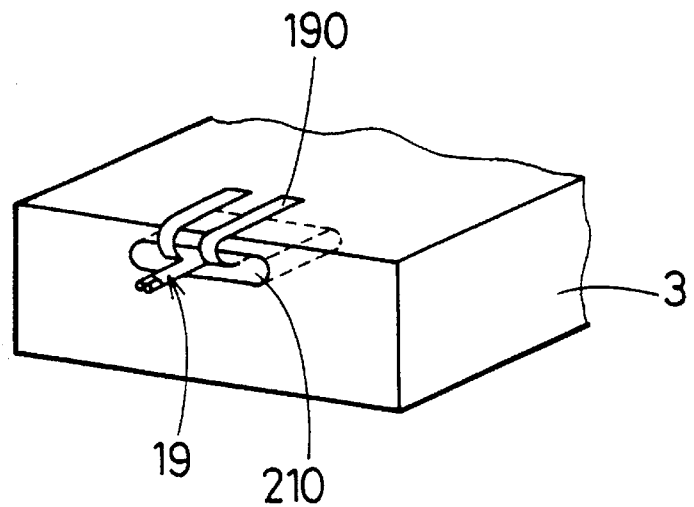
FIG. 14 is an explanatory view showing the fitting/ contacting state of the contacting fixture of Embodiment 7.

In the present embodiment, as shown in FIG. 13, the elastic contacting portion 190 of a contacting fixture 19 is formed into a clip shape which has its upper and lower faces to contact with the cylindrical contact. The elastic contacting portion 190 is retained between the flattened cylindrical engaging entrance 210 and the surface of the base member 3, as shown in FIG. 14.

Embodiment 8

An oxygen sensor will be described as one embodiment of the gas sensor of the present invention with reference to FIGS. 15 to 20.

Figure 15:
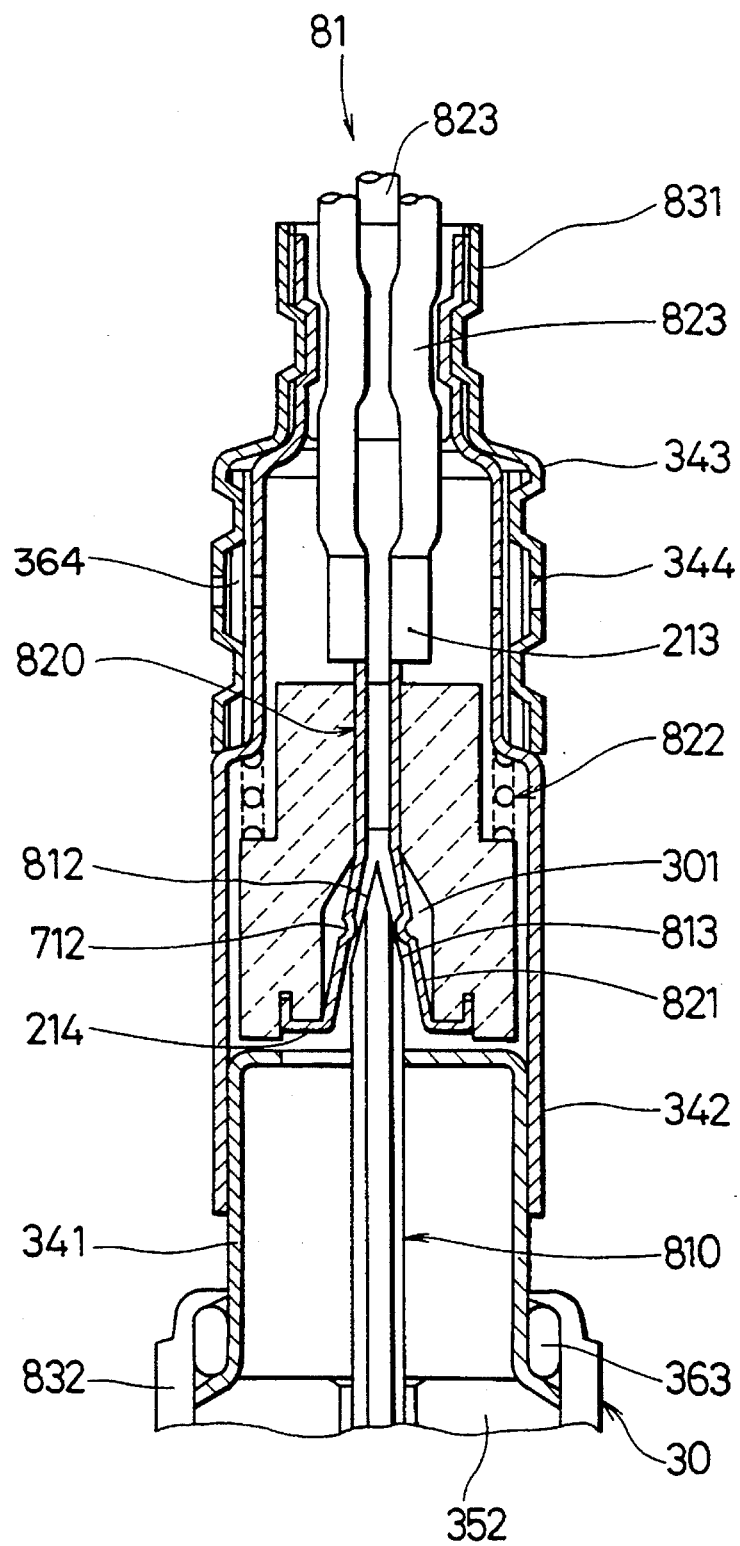
FIG. 15 is a section view of an essential portion of an oxygen sensor of an embodiment.
Figure 16:
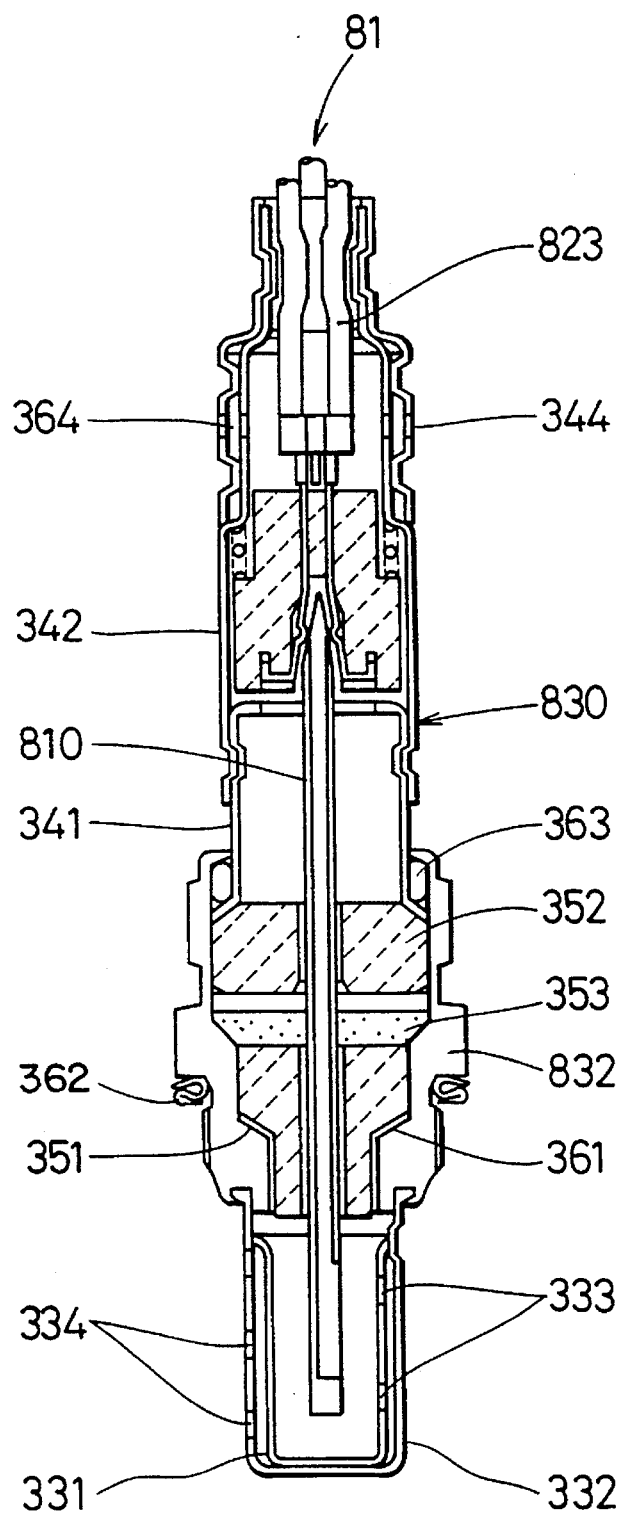
FIG. 16 is a section view of the oxygen sensor of the embodiment.

In the present embodiment, as shown in FIGS. 15 and 16, an oxygen sensor 81 is constructed to include: an elongated oxygen detecting element 810 for producing an output corresponding to an oxygen concentration; a cylindrical housing 830 mounting the oxygen detecting element 810 in its leading end side; and an external connection member 820 adapted to contact in the housing 830 with electric terminal portions 813 of the oxygen detecting element 810 for inputting/outputting electric signals from the base end portion 831 of the housing 830.

Figure 17:
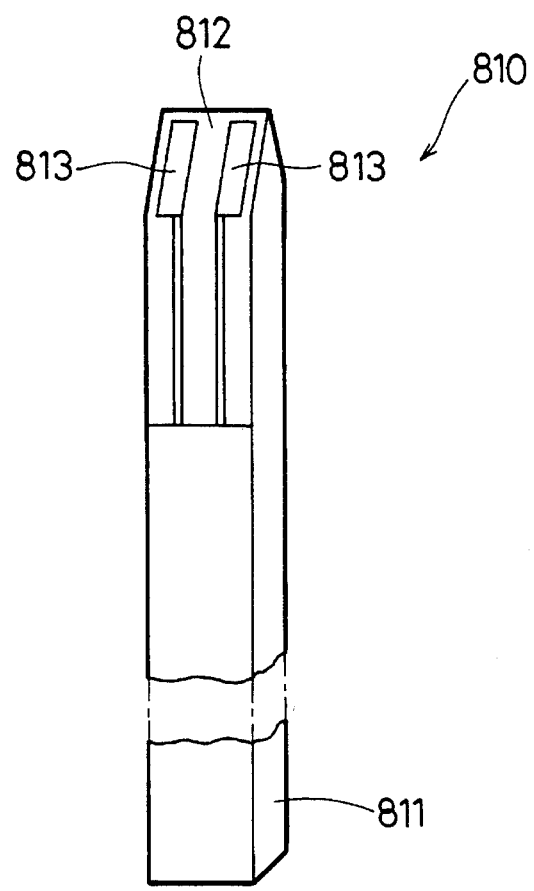
FIG. 17 is a perspective view of an oxygen detecting element of an embodiment.

The oxygen detecting element 810 is composed, as shown in FIG. 17, of a detecting portion 811 formed at the leading end side, and the electric terminal portions 813 arranged on a taper face 812 formed at the base end portion.

Figure 18:
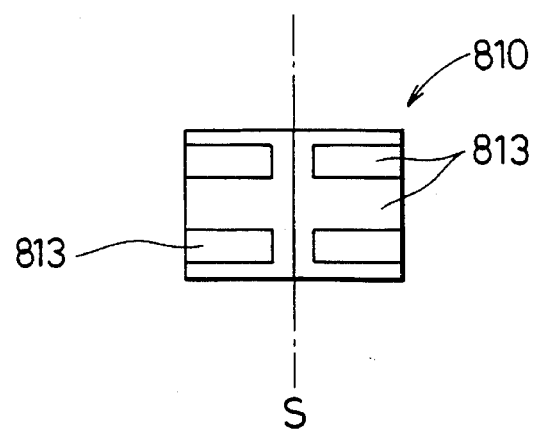
FIG. 18 is a top plan view of FIG. 16.

This taper face 812 is formed to approach an axial plane S (i.e., a plane extending on the axis) (of FIG. 18) toward the base end portion and to be symmetrical with respect to the axial plane S, and the electric terminal portions 813 are arranged on the taper face 812 symmetrically of the axial plane S, as shown in FIG. 18.

Figure 19:
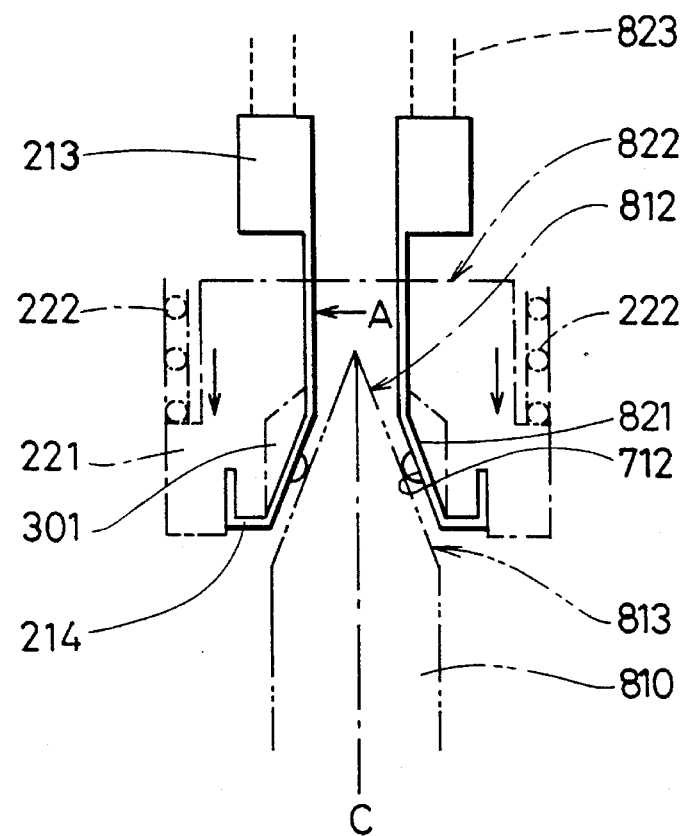
FIG. 19 is a front elevation view of a contact in the embodiment.

On the other hand, the external connection member 820 is equipped, as shown in FIG. 19, with: contacts 821 likewise arranged symmetrically to face the electric terminal portions 813; and a thrust member 822 thrusting the contacts 821 toward the leading end.

The contacts 821 are made of highly elastic members extending in the axial direction C. As shown in FIG. 15, the housing 830 is formed therein with a clearance 301 for allowing the leading end portions of the contacts 821 to curve toward the inner wall of the housing 830.

Figure 20:
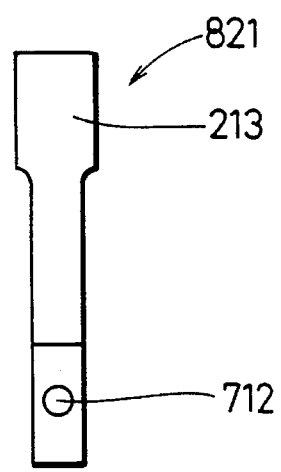
FIG. 20 is a side elevation view of the contact of FIG. 18, as viewed in the direction of arrow A.
Figure 21:
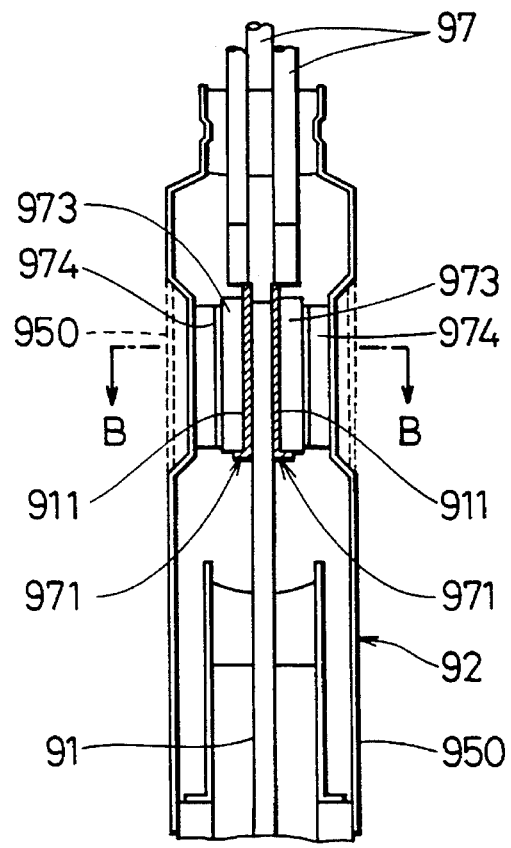
FIG. 21 is a section view of an essential portion of an oxygen sensor of the prior art.
Figure 22:
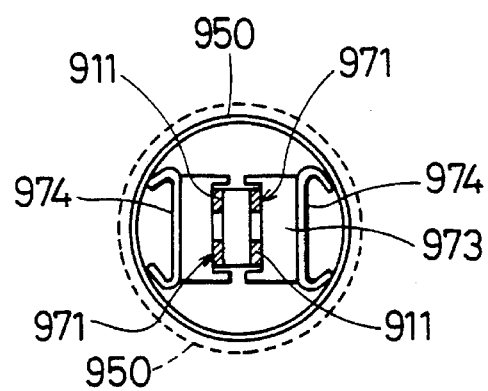
FIG. 22 is a section view of FIG. 21 as taken in the direction of arrow B.

As shown in FIGS. 19 and 20, on the other hand, the contacting face of each contact 821 with the corresponding electric terminal portion 813 is formed with a bulging portion 712 to abut against the electric terminal portion 813.

These components will be individually described in detail in the following.

The present embodiment is directed to the oxygen sensor 81 for detecting the air/fuel ratio of an automotive engine.

The housing 830 is composed, as shown in FIG. 16, of: a drum portion 832 for mounting the oxygen sensor 81 in the exhaust passage of the engine; element covers 331 and 332 to be inserted into the exhaust passage; and protective covers 341, 342 and 332.

These element covers 331 and 332 are divided into the internal cover 331 and the external cover 332, which are formed with exhaust ports 333 and 334 for introducing the exhaust gas.

On the other hand, the third protective cover 343, as located at the base end portion, is formed with an air vents 344 for introducing the atmosphere into the oxygen detecting element 810.

The oxygen detecting element 81 is held in the drum portion 832 through insulating members 351 and 352, between which is arranged a powder seal member 353 for fixing the element and sealing the exhaust gas.

In FIG. 16, reference numeral 361 designates a washer; numeral 362 a gasket; numeral 363 a metallic ring; and numeral 364 a dust proofing filter.

The oxygen detecting element 810 is formed into an elongated rectangular member by integrally laminating the not-shown plate-shaped solid electrolyte element, air introducing member and insulating sheet. Moreover, the oxygen detecting element 810 is equipped with a conducting member for the electric heater and a pair of electrodes, which are electrically connected with the electric terminal portions 813.

The external connection member 820 is integrally equipped with the contacts 821 and lead wires 823, as shown in FIG. 15, and is fixed by a caulking portion 213. Each contact 821 is formed, as shown in FIGS. 19 and 20, with a contact portion to contact with the corresponding electric terminal portion 813 having the bulging portion 712, and a caulking portion 213 to be connected with a lead wire 823 by the pressing method.

This caulking portion 213 is pressed while carrying the bare portion of the lead wire 823.

The thrust member 822 is composed, as shown in FIG. 19, of a retaining portion 221 for retaining the corresponding contact 821, and a coil spring for thrusting the retaining portion 221 toward the leading end.

On the other hand, each contact 821 is formed at its leading end with a hook-shaped bent portion 214, which has its leading end portion fitted and retained in the groove of the retaining portion 221.

Here will be described the operations and effect of the present embodiment.

In the oxygen sensor 81 of the present embodiment, as shown in FIG. 19, the thrust member 822 thrusts the contacts 821 in parallel with the axis C toward the electric terminal portions 813 arranged on the taper faces 812.

Since, moreover, the contacts 821 are arranged symmetrically with respect to the axis C, the transverse loads upon the oxygen detecting elements 810 are balanced so that only the longitudinal load is applied to the oxygen detecting element 810.

Moreover, this oxygen detecting element 810 is so elongated in the longitudinal direction that it has remarkably high durability against the longitudinal load. As a result, the contacts 821 can be forced into reliable contact with the electric terminal portions 813.

Moreover, the thrust of the contacts 821 to be established can be remarkably high because it is generated by the thrust member 822 which is separate from the contacts 821. This is because the housing 830 is so elongated to give a degree of freedom to the space to be arranged with the coil spring 222.

On the other hand, the electric terminal portions 813 are inclined with respect to the axis so that the contacts 821 thrust toward the leading end are brought into the electric terminal portions 813 without fail.

Moreover, the thrust is concentrated at the bulging portions 712 formed on the contacts 821, so that the pressure to contact the electric terminal portions 813 is raised to ensure their electrical conductivity.

On the other hand, the contacts 821 are highly elastic members so that they can be bent onto the inner wall of the housing 830 without establishing excessive contacting force.

In case, moreover, the contacts 821 are deformed by creep, they are further bent toward the inner wall by the thrust of the thrust member 822 so that their contacting pressure with the electric terminal portions 813 can be kept at a substantially constant level.

As described above, the contacting relation between the electric terminal portions 813 and the contacts 821 is so stable for a long time that it is highly reliable.

Here, the electric connections between the electric terminal portions 813 and the contacts 821 need not resort to a process requiring many steps, such as the soldering process.

As described hereinbefore, according to the present embodiment, the oxygen detecting element 810 can have its electric connections effected between its electric terminal portions 813 and the external connection members 820 by the contacting method allowing a feasible assembly, to provide the oxygen sensor 81 having a high contact reliability.

What is claimed is:

1. A gas sensor comprising:

a base member;

a detecting unit mounted on said base member for detecting a gas concentration;

electrodes mounted on said detecting unit; cylindrical contacts buried integrally in an end portion of said base member;

and electric leads interposed between said cylindrical contacts and said electrodes, and contacting fixtures for external lead wires fitted in and contacted with said cylindrical contacts so that they are connected with the cylindrical contacts.

2. A gas sensor according to claim 1, wherein said cylindrical contacts are formed in their openings with engaging entrances having a smaller diameter than the internal diameter, and wherein said contacting fixtures include elastic contacting portions adapted to be diametrically reduced, when inserted into said cylindrical contacts, than said engaging entrances and expanded, after inserted, to become larger than said engaging entrances and to contact with the inner walls of said cylindrical contacts.

3. A gas sensor according to claim 2, wherein said cylindrical contacts have a shape of a cylindrical or polygonal cylinder.

4. A gas sensor according to claim 1, wherein said contacting fixtures are in close contact with inner walls of said cylindrical contacts substantially all over their outer circumferences.

5. A gas sensor according to claim 1, wherein said contacting fixtures are fitted in and contact with said cylindrical contacts by radially outward forces from said contacting fixtures to said cylindrical contacts.

6. A gas sensor according to claim 1, wherein said cylindrical contacts are tubular contacts.

7. A method of manufacturing a gas sensor comprising a base member, a detecting unit mounted on said base member for detecting a gas concentration, electrodes mounted on said base unit, cylindrical contacts buried integrally in an end portion of said base member, and electric leads interposed between said cylindrical contacts and said electrodes, and contacting fixtures for external lead wires fitted in and contacted with said cylindrical contacts so that they are connected with the cylindrical contacts, said method comprising the step of:

integrally burying said cylindrical contacts in the end portion of said base member by an injection molding process.

8. A gas sensor comprising:

an elongated oxygen detecting element having a detecting unit at one end and having electric terminal portions having taper faces having their distances gradually reduced from the axis or axis plane toward the other end at the other end of said detecting element, for producing an output corresponding to an oxygen concentration;

a cylindrical housing accommodating said oxygen detecting element;

and external connection means having contact portions formed in said housing and opposed to said electric terminal portions, and a thrust portion for thrusting said contact portions toward said leading end, so that said external connection means is brought into contact with the electric terminal portions of said oxygen detecting element by said contact portions and said thrust portion, to input/output electric signals from the other end of said housing;

whereby a component of thrust from said thrust portion is directed perpendicular to an axis of said element and a component of thrust from said thrust portion is directed parallel to said axis of said element, an amount of said thrust directed perpendicular to said element axis being less than a total amount of thrust from said thrust portion.

9. A gas sensor according to claim 8, wherein said electric terminal portions are arranged symmetrically on said taper faces with respect to the axis of axial plane.

10. A gas sensor according to claim 8, wherein the contact portions of said external connection means are so symmetrically arranged as to face said electric terminal portions.

11. A gas sensor according to claim 8, wherein said contact portions are conductive, highly elastic members extending in the axial direction, and wherein said housing is formed with a clearance in which the front ends of said contact portions can be bent toward the inner wall of said housing.

12. A gas sensor according to claim 8, wherein the contact faces of said contact portions with said electric terminal portions are rugged to abut against said electric terminal portions.

13. An oxygen sensor comprising:

an elongated oxygen detecting element for producing an output corresponding to an oxygen concentration;

a cylindrical housing for accommodating said oxygen detecting element at its leading end; and an external connection member contacting with the electric terminal portions of said oxygen detecting element in said housing for inputting/outputting electric signals from the base end of said housing, wherein said oxygen detecting element includes a detecting unit formed at its leading end, and electric terminal portions arranged on taper faces formed at the base end, wherein said taper faces have their distances gradually reduced from the axis or axial plane toward said base end, wherein said electric terminal portions are arranged on said taper faces symmetrically with respect to the axis of axial plane, and wherein said external connection members have contacts opposed to said electric terminal portions and likewise arranged symmetrically, and a thrust member for thrusting said contacts toward said leading end.

14. An oxygen sensor according to claim 13, wherein said contacts are made of conductive, highly elastic members extending in the axial direction, and wherein said housing is formed therein with a clearance in which the leading ends of said contacts can be curved toward the inner wall of said housing.

15. An oxygen sensor according to claim 14, wherein the contact faces of said contacts with said electric terminal portions are formed with bulging portions to abut against said electric terminal portions.

* * * * *